United States Patent [19]
Rebiere

[11] Patent Number: 6,160,264
[45] Date of Patent: Dec. 12, 2000

[54] SYSTEM FOR PLOTTING A TRI-DIMENSIONAL SHAPE, NOTABLY A PLANTAR ARCH, AND METHOD OF OPERATING THE SYSTEM FOR PRODUCING AN ORTHOPAEDIC SHOE OR SOLE

[75] Inventor: Christian Rebiere, Caraman, France

[73] Assignee: Kreon Industrie, Limoges, France

[21] Appl. No.: 09/295,331

[22] Filed: Apr. 21, 1999

[30] Foreign Application Priority Data

Apr. 21, 1998 [FR] France .................................. 98-04981

[51] Int. Cl.⁷ .................................................. G01B 11/24
[52] U.S. Cl. .................... 250/559.22; 33/33 A; 33/33 C; 33/552; 12/142 N; 12/146 M; 12/1 R
[58] Field of Search ............................ 250/559.22, 559.33; 33/3 A, 3 B, 3 C, 514.2, 512, 552; 12/142 N, 146 M, 1 R

[56] References Cited

U.S. PATENT DOCUMENTS

| 4,876,758 | 10/1989 | Rollof et al. ............................ 12/146 M |
| 5,015,429 | 5/1991 | Suzuki ..................................... 264/138 |
| 5,424,835 | 6/1995 | Cosnard et al. ........................ 356/376 |
| 5,689,446 | 11/1997 | Sundman et al. ........................ 364/560 |

FOREIGN PATENT DOCUMENTS

| 285989 | 10/1988 | European Pat. Off. . |
| 2685764 | 7/1993 | France . |
| 940079 | 5/1995 | Germany . |
| 9716800 | 5/1997 | WIPO . |

*Primary Examiner*—F. L. Evans
*Attorney, Agent, or Firm*—Millen, White, Zelano & Branigan

[57] ABSTRACT

The system (7) for plotting the shape of a tri-dimensional object (2) is used in particular for the profile of a plantar arch (20). It comprises a sensing device (1) having rods (3) movable in a support (10, 11) such that said object (2) can be applied onto the first end (300) of each of said rods under a determined pressure force so as to drive said rods (3) in a translation motion and such that the set of the second ends (301) of said rods (3) define a surface ($S_A$) replicating said shape to be plotted (20). Spring means (4) are associated with said movable rods (3) to oppose a calibrated resilient force opposing said pressure force. The system further comprises a contactless acquisition device (5) for acquiring and digitalizing said surface ($S_A$) replicating said shape to be plotted (20), said device (5) delivering output electric signals ($V_S$) correlated with the space coordinates of said second end (301) of said rods (3), with respect to reference coordinates ($P_R$) defined by the position taken by the rods in a so-called rest state.

21 Claims, 5 Drawing Sheets

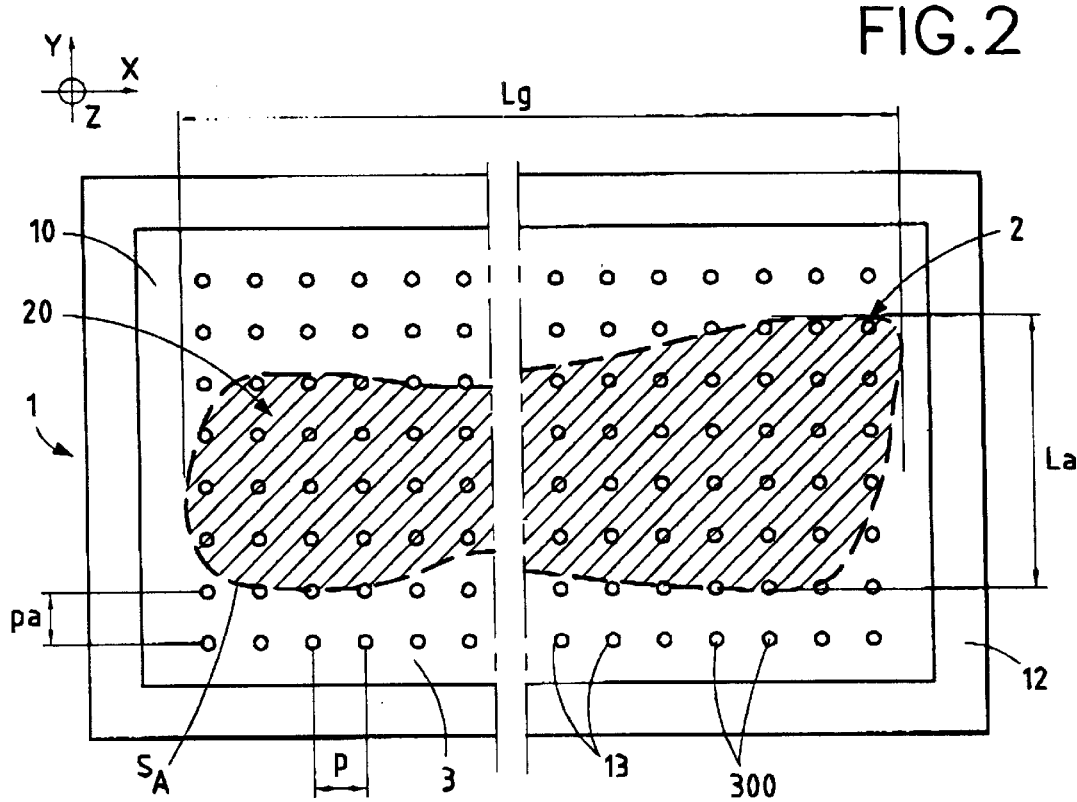
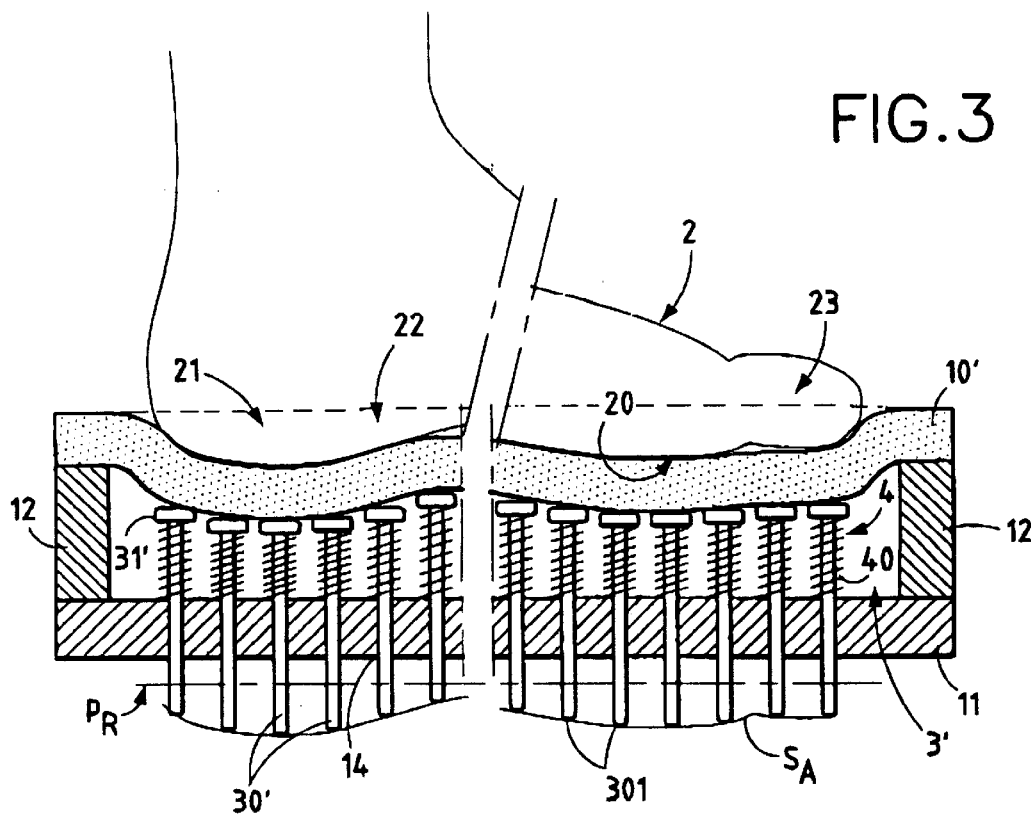

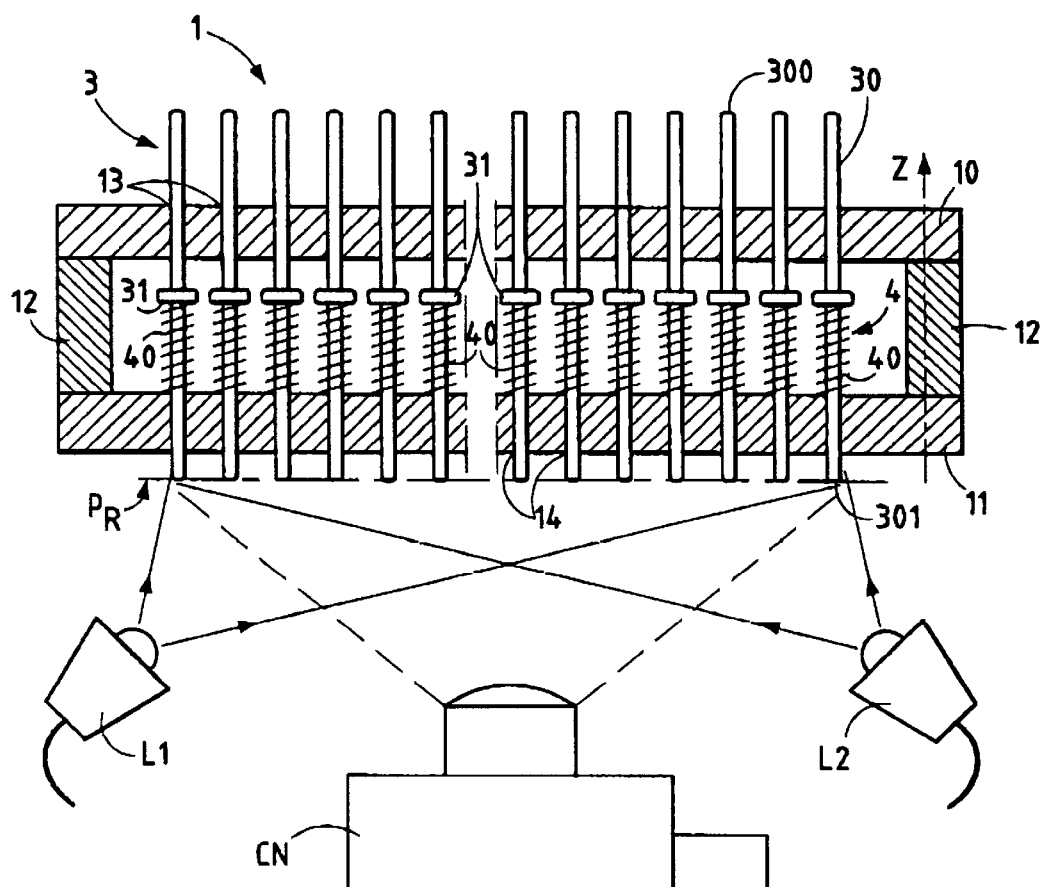
FIG.6A
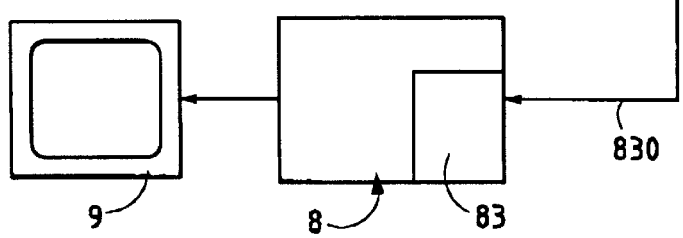
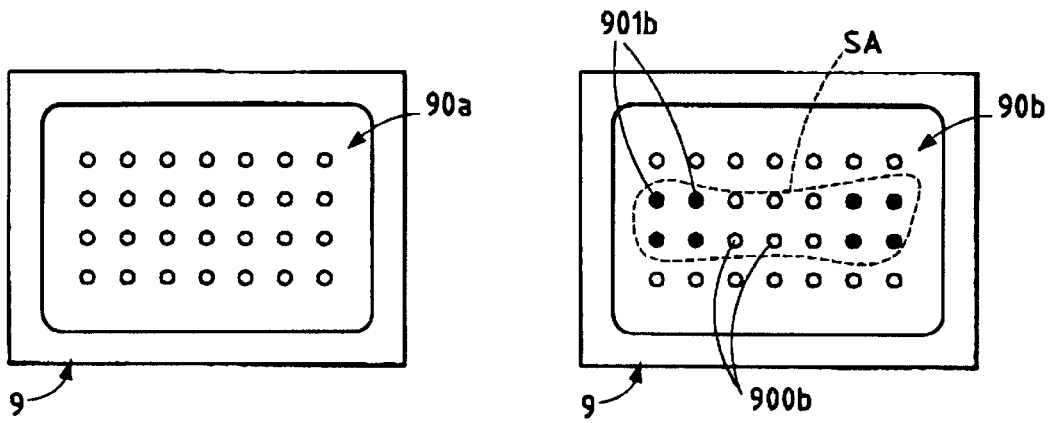
FIG.6B  FIG.6C

SYSTEM FOR PLOTTING A TRI-DIMENSIONAL SHAPE, NOTABLY A PLANTAR ARCH, AND METHOD OF OPERATING THE SYSTEM FOR PRODUCING AN ORTHOPAEDIC SHOE OR SOLE

FIELD OF THE INVENTION

The present invention relates to a system for plotting a tri-dimensional shape. It relates more particularly, but not exclusively, to a system for plotting the shape of a foot plantar arch. Such a system is, for instance, used for producing customized shoes.

More specifically, it concerns a method for producing orthopaedic shoes or soles using such a system. To clarify the present disclosure, and without this limiting in any way the scope of the invention, the following description will be made within the frame of this preferred application.

For an application of this type, it is necessary to know the shape of a plantar arch of one or both feet of a user or patient, in order to produce orthopaedic customized shoes or, at least, accessories such as soles for such shoes.

BACKGROUND OF THE INVENTION

Many methods or devices are implemented in the present art, which can arbitrarily be classified into two main categories.

A first category consists of devices or methods which can be qualified as analogical. It is possible for instance to mould the foot shape. The user lays his foot on a block of malleable, silicone-based for instance, material. Because of the exerted pressure, the material block will keep the footprint shape and can be used as a matrix for later production of an orthopaedic shoe or sole.

The precision obtained by this method is not very high. Furthermore, passing the thus acquired matrix to the end product, i.e. the shoe or sole, is neither easy nor quick to perform. The method requires a large number of manual steps.

Furthermore, not only one but generally several footprints need be obtained, in order to optimally simulate various physical states: foot laying (flat), foot resting on the tip, and foot resting on the heel, for instance, which makes the process more complex.

The second category includes digital devices and methods.

Many systems with optical sensors are known, in particular the system disclosed by the applicant's French Patent FR 2 685 764 entitled: "Capteur optique compact et à haute résolution pour l'analyse de formes tri-dimensionnelles", i.e. "A compact, high resolution optical sensor for analyzing tri-dimensional shapes". That system allows acquiring tri-dimensional pieces having a warped surface and digitizing them. For that purpose, the system includes an optical sensor with a laser beam source and one or more cameras analyzing the trace formed by the laser beam on the object to be studied.

Stating it more precisely, the system generates a so-called laser "plane", i.e. a very thin sectoral lamellar beam with a width that allows it to cover either all or part of the object to be analyzed, with the above cameras observing the beam trace under different incidence angles. Acquisition and digitalization are performed by scanning the object surface by the laser light plane.

In the case of the applications aimed at by the invention, such an optical sensor system cannot be used as it is for acquiring and digitalizing the profile of a foot arch, mainly because the surface the profile of which is to be plotted is located underneath the foot, and therefore cannot be accessed to, inasmuch as it should be observed while the patient is standing or walking.

That precludes taking full profit from the advantages the optical sensing devices can exhibit on the other hand, through allowing to reach a high resolution in the three-dimensional profile made to a set of points, or does, with known coordinates with respect to a referential (usually a horizontal plane), and through ensuring a rapid acquisition with a high precision, as well as through performing the digitalization of the acquired shape, which allows an immediately or delayed exploitation of the obtained measurements. Namely, the acquired data can be processed by a computer with a pre-recorded program for delivery to an exploiting device (digital control machine tool for instance), and/or viewed, and/or stored in a mass memory for later in situ or remote use.

The obtained result however also depends upon the exact conditions in which the acquisition is performed. The foot namely needs to be in conditions as close to reality as possible. It consequently has to rest on a support surface and the arch of this foot should not be deformed by this support surface, since such would falsify the measurements. The acquisition must be performed from below, i.e. in a practical manner through a transparent wall, for instance a thick glass wall. The foot clearly may not move, once it rests on the transparent support surface. Obtaining the above mentioned scanning therefore requires the beam to be moved with respect to the foot, either by deflection or by a physical movement of the sensor (translation motion).

The presence of a wall, even a transparent one, is not without inconveniences since it will produce deviations (by refraction) of the generated beam or beams, when crossing back and forth (after reflection on the surface of the foot arch). Furthermore, the transparent material may include impurities inducing stray deviations and/or diffraction during scanning. Finally, since the acquisition must be performed in conditions as close to reality as possible, the wall may not be planar, it should simulate the internal shoe surface, which introduces deformations of the generated beam or beams, which will vary during this scanning process.

To solve the above stated problems, the applicant has proposed, in a French patent published under number 2735859 entitled "Procédé d'acquisition et de numérisation d'objets au travers d'une paroi transparente et système de mise en oeuvre d'un tel procédé", i.e. "A method for acquiring and digitalizing objects through a transparent wall and system for implementing such a method", a system comprising several optical sensors surrounding a tri-dimensional object, the shape of which is to be acquired. Each sensor preferably is of a type described in the patent FR-B-2 685 764 and includes a laser source emitting a lamellar planar beam. The set of the laser planes is coplanar, so as to form a single measurement plane. The full shape of the foot can be acquired by successive slices, with each slice being obtained in an almost instantaneous manner, without requiring any rotation of the sensor system around the longitudinal axis of the foot. Acquiring the different slices only needs a translation motion parallel to this axis.

During a preliminary phase, the measurement space is calibrated and the upper and lower surfaces of the transparent wall are acquired and digitized, which allows eliminating the stray influence of this wall (curvature, defects, and so on).

Although this system offers many advantages, and particularly for producing customized shoes, since it allows acquiring and digitizing the full foot shape in just one run, it does not fully meet the needs that appear in the frame of the applications the invention is aiming at, in particular for producing orthopaedic accessories.

Using a transparent wall with a non planar surface, which simulates the internal surface of a shoe, namely only constitutes, at best, a compromise solution. The foot namely rest on a wall with a pre-established shape, whereas only the foot should itself impose a shape to this wall. The shape which should be acquired namely is that of the plantar arch, without any constraint whatsoever. Furthermore, as previously indicated, various positions of the plantar arch should successively be acquired: foot laying (flat), foot resting on the heel and/or on the tip, for instance. A single support shape is not sufficient.

Finally, other requirements are associated with a system used for the preferably considered applications of the invention: simplicity, easy handling, easy transportation of the equipment for plotting the shape of a tri-dimensional object.

SUMMARY OF THE INVENTION

The invention is aiming at overcoming the defects of the prior art devices, while keeping the advantages inherent to a system with an optical sensor, including the fact that the measurements are performed without contact with the sensing parts.

For this purpose, the system of the invention for plotting the shape of a tri-dimensional object includes a sensing device, comprising a frame or box supporting a matrix of elastically retractable needles, or rods, on top of which the plantar arch rests. Because of the exerted vertical force (due to the weight of the user), the needles will be pushed downward or, in other terms, will move in downward translation along themselves. The needles are associated with resilient resisting means such as calibrated springs so as to control that plunging movement.

The set of needles at their opposite bottom ends reproduce the exact profile of either the foot arch or the part of the arch resting on top of the needles, whatever the adopted posture is: foot laying (flat) or resting on the tip or on the heel. More generally, if any tri-dimensional objects exert a pressure force on the first ends of the needles, the profile of the support face is reproduced by the set of the second ends of the needles. Saying so, it is considered that all needles have same length, but this is not compulsory.

The system of the invention finally includes a shape acquisition device, arranged below the needle sensor device, so as to acquire a dot chart representing the profile or the surface formed by the lower ends of the needles and to perform their digitalization.

According to a first embodiment of the invention, the system comprises a shape acquisition and digitalization device consisting of an optical sensor wherein at least one opto-electronic camera and at least one laser source are implemented. The plotting results from a scanning of the lower surface drawn by the bottom end of the needles using at least one laser beam. The output signals generated by the optical sensor, which represent data of the dot chart coordinates, are then transmitted to a signal processing member, possibly after preliminary digitalization. The acquired data may be readily exploited by any proper device (such as a digital control machine tool, or similar) and/or stored for later use.

When the pressure force is released, the needles revert to their rest position by being pushed back by the spring means.

In this so-called "rest" "position" (before and after acquisition), the set of the lower needle ends constitutes a surface which can be used as a reference for an initial calibration of the optical sensor device. Generally that surface is substantially a plane parallel to the planar surface of the upper ends and it is disposed horizontal most often.

According to a second embodiment, an imaging device is operated. The shape acquisition results from a photo-camera or a digital video camera. The lower needle ends are illuminated by a light source. The amount of the plunge can be determined by means of the light density variations. The electronic signal output by the photo camera or the digital camera are transmitted to a digital acquisition board within a microcomputer or similar, and are processed with the help of an image processing software.

According to a third embodiment, which itself can present several versions, an optical or magnetic telemetry device is operated. The telemetry device, which can be based on an array of semiconductor laser diodes, is placed below a needle matrix. The telemetry device measures the distance separating it from each of the lower need ends, and thus can determine the plunge with respect to a reference plane.

According to a preferred alternative of the system of the invention, which can be used in combination with any of the above optical acquisition device means, the sensing device is provided with means to vary the calibration of resilient means opposing a predetermined force to the downward movement of the needles, and take into account thereby the user's weight and morphology. In one of the embodiments of the invention, several distinct sensing devices are used, each comprising a specific set of needles associated with respective calibrated springs, such as can be provided by helicoidal springs wound around each needle and extending lengthwise compressed against a stop integral with the needle. In such case, the resisting action of the springs is determined by their initial compression.

In a preferred embodiment however, the sensing device itself is provided with means to vary said initial compression and adapt the spring strength to the user's weight so that a measurable displacement of the needles is always ensured and the surface determined by their lower ends is a correct duplicate of the foot arch profile. That result can be advantageously reached through a movable plate onto which the individual springs are in abutment at one end while their other ends are fixed. In a specific embodiment, the springs extend from a fixed bottom plate of the support having bores for the passage of the needles up to a movable plate that is also provided with guiding bores or holes for the needles. The abutment of the springs can be controlled by stops individually integral with each needle. The needle calibration obtained thereby can be set to a number of predetermined positions of the moving plate, corresponding for instance to three different strength values to be selected for each person depending on age and weight.

The invention consequently relates to a system for plotting the profile of a tri-dimensional object, in particular for determining the profile of a foot plantar arch, that comprises a sensing device comprising a matrix of rods movable across a support for receiving said object onto a first top end of each said rods under a determined pressure force, thereby driving said rods in a translation motion through a distance varying from one rod to another depending on said profile shape so that the second bottom ends of said rods define together a surface duplicating said profile shape to be plotted, resilient means being associated with said movable rods to oppose a predetermined resisting force opposing said pressure force, and further comprises a contactless acquisition device for acquiring and digitalizing said surface duplicating said shape to be plotted, wherein said device delivers output electric signals correlated with the space coordinates of said second end of said rods with respect to reference coordinates defined by the position taken by the rods in a rest state.

The invention further relates to a method for producing orthopaedic shoes and soles using the above system.

BRIEF DESCRIPTION OF THE DRAWINGS

The invention will be better understood, and further features and advantages will become clear, upon reading the following description while referring to the appended figures in which:

FIG. 2 is a bottom view of this same device;

FIG. 3 illustrates an alternative of the sensing device of FIGS. 1A to 2;

FIGS. 6A–6C illustrate a shape acquisition and digitalization device according to a first additional embodiment;

DETAILED DESCRIPTION OF PREFERRED EMBODIMENTS

Figure 1A:
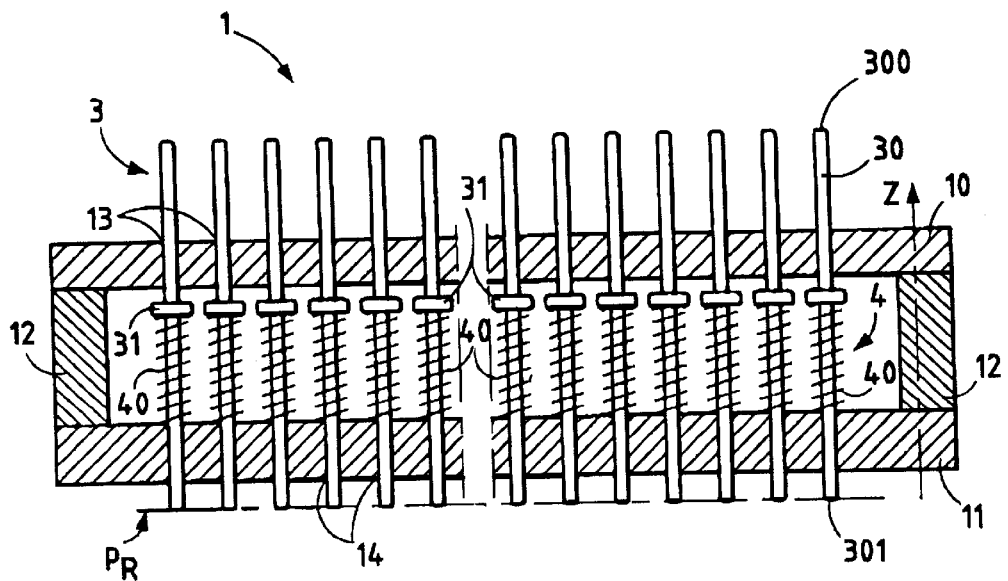
FIGS. 1A and 1B are a cross section and a side view of an embodiment of a sensing device with needles and calibrated springs, constituting one of the component of the system for plotting a foot arch according to the invention, both at rest and during shape acquisition measurements, respectively.

An embodiment of a system for detecting and registering the profile data of a foot arch surface according to the invention will now be described, starting with an embodiment of one of the essential components it comprises, namely the sensing device 1 as shown on FIGS. 1A, 1B, and 2.

The sensing device 1 consists of a box or other kind of structural support 1 for retractable sensing members illustrated as a matrix of movable needles made of rods resiliently urged upwards by spring means against the vertical force exerted downwards on their upper ends due to a person standing on them.

The structure of the needle box 1 essentially includes walls, which arbitrarily will be called upper 10 and lower 11 walls, or main parallel walls, that are maintained at a constant distance from one another by lateral walls or spacers 12. The upper 10 and lower 11 walls have through holes 13 and 14, respectively, and advantageously are substantially planar. These holes, 13 and 14, leave a free passage for the cylindrical bodies 30 of a set of needles or rods 3, so that these cylindrical bodies 30 can be translated along their axis parallel to a direction Z orthogonal to both walls 10 and 11, a priori a vertical axis in the preferred application. The upper ends 300 and the lower ends 301 of the cylindrical bodies 30 protrude from the upper 10 and lower 11 walls, respectively.

The cylindrical bodies 30 bear limit stops 31 near the upper wall 10. A set 4 of springs 40, arranged between the lower wall 10 and those limit stops 31, forces the needles 3 back upward (in the example of FIG. 1A). The springs 40 are coaxial with the cylindrical bodies 30. In a so-called rest state, illustrated in FIG. 1A, i.e. when no pressure force is exerted on the upper ends 300 of the needles 3, these needles are in the hereafter called high position. The set of lower ends 301 of these needles 3 forms altogether a substantially planar surface which defines a reference plane $P_R$. The device can in fact be arranged in such a way that the limit stops 31 contact the lower face of the upper wall 10, so that the needle rest positions are well defined. If the flatness of that face is good, the reference plane $P_R$ is also defined with a good precision.

Preferably, and so more particularly illustrated in FIG. 2 which shows the device 1 in a top view, the needles 3 are regularly distributed at the intersections of columns and rows of a rectangular matrix, i.e. with two orthogonal axes X and Y, both of which in their turn are orthogonal to the above mentioned Z axis.

When the (non-represented) user lays his foot 2 on the needles 3, or more precisely on the upper ends 300 thereof, the needles are pushed downwards parallel to their own axis due to the exerted pressure. According to an important feature of the invention, this displacement is performed in a controlled manner, due to the action of the set 4 of calibrated springs 40. Since the latter are imprisoned between the lower wall 11 and the limit stops 31, they will be compressed to a larger or smaller extent depending upon the amount of the pressure force locally exerted on any particular needle 3. The calibration can be obtained, either intrinsically by using springs with a predetermined rigidity, or by exerting a pre-stress such that the springs already are compressed in their rest state (FIG. 1A) between the limit stops 31 and the lower wall 11.

Figure 1B:
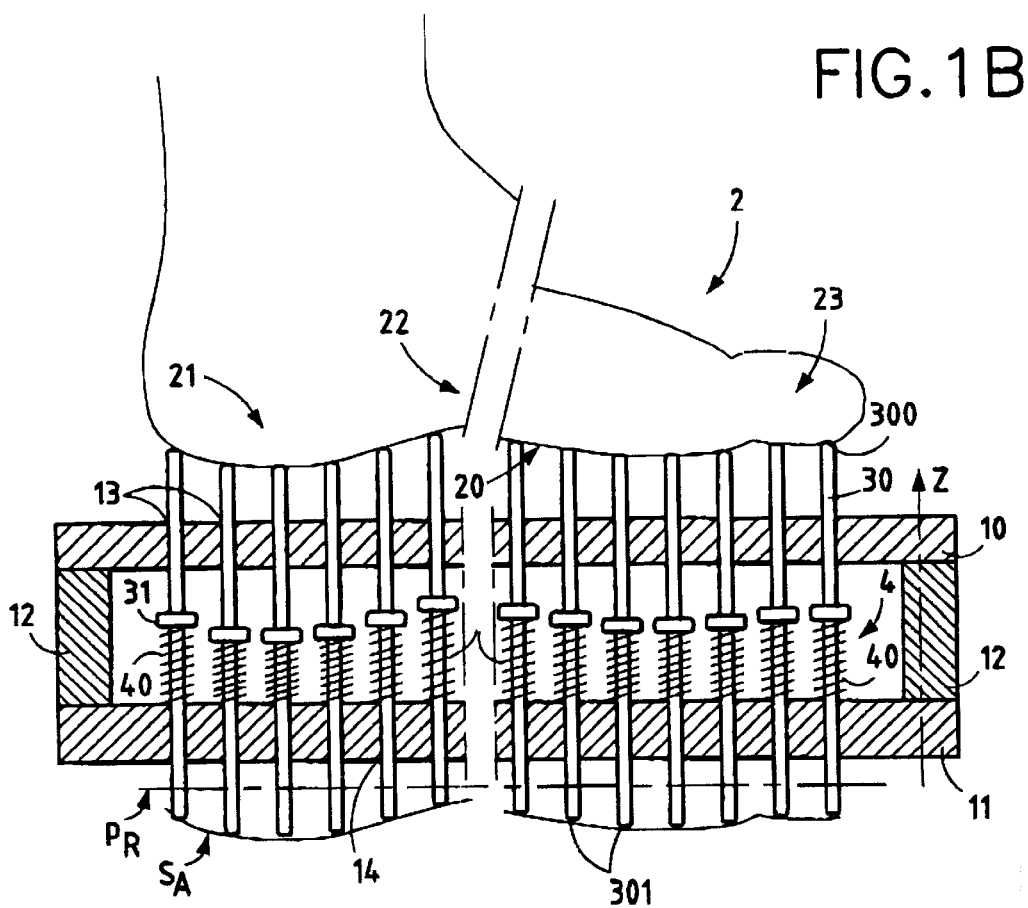

As an example, and as illustrated by FIG. 1B, when the foot 2 lays flat on the set of needles 3, the heel 21 (left part of FIG. 1B) exerts a higher compression force than the foot tip 23 (right-hand side). The central part 22 of the plantar arch 20, being recessed further up, exerts an even lower pressure force. As a result, the lower ends 301 of the needles 3 will protrude to a larger or smaller extent from the lower wall 11. The set of these ends 301 of the needles 3 will, by interpolation, define a surface $S_A$ that reproduces the bottom of the foot 2, i.e. the profile of the plantar arch 20, the acquisition of which is desired.

It should be noted that at least at the initial instant when the foot 2 lays on the device 1 with all springs 40 opposing an identical resistance to the pressure force, the reproduction mentioned above is faithful, since the profile of the support surface (upper ends 300 of the needles 3) is determined by the profile of the plantar arch, and not conversely as would be the case if the support surface profile happened to be pre-established. The specific arrangements of the invention consequently afford a remedy to the above mentioned drawbacks caused by the optical sensor systems of the prior art.

In order for the shape acquisition to be performed with a good precision, a sufficient number of needles 3 is provided. An insufficient number of needles would falsify the measurement for a further reason: since the living material of the foot is malleable, the superficial plunge of the various needles 3 would differ from one place of the plantar arch 20 to the other, depending upon the exerted local pressure. The error factor is minimized when the number of the needles 3 increases. It finally is clear that the shape acquisition process should not cause any discomfort and especially no pain for the user, as would be the case if the number of needles 3 happened to be insufficient.

For the device 1 to be convenient for different users, the adjustment of the repulsion force of the springs 40, in other words their calibration, needs furthermore to be adapted to the user's weight and morphology.

For this purpose, two main schemes can be used.

According to a first scheme, a range of interchangeable sensing devices is used. As a practical example, three distinct models of distinct devices can be conceived: a first model designed for the adults, a second one for the children and juniors, and a third one for the very young children, possibly babies. The dimensions of the device 1, particularly the number of needles 3 and mostly the specific calibration of the springs 400, will vary from one model to the next.

According to the second scheme, a single needle box model is used for all user ages and weights. In such a case, the strength of the resisting springs, in other words the spring calibration, is adjustable. A pre-stress can for instance be applied. The latter can be obtained and adjusted by moving the upper 10 and lower 11 walls closer to or further from one another, with the help of an adjustable thread system replacing all or part of the side walls 12. The springs stay arranged between the limit stops 31 and the lower wall 11. The calibration of the whole needle rods is thereby varied simultaneously.

One can also, and preferably according to the invention, provide the so-called box 1 with an intermediate plate slidably mounted on the lateral walls 12 or equivalent tie-bars so as to receive the stops 31 in abutment thereon. It is then sufficient to adjust the position of that plate to obtain the desired calibration. Optionally, predetermined calibration positions can be provided, for instance for an adult of relatively high weight, for a light slim adult or junior, for a child. The place can be set a any of three corresponding levels using, for instance, a hand-controlled cam system acting simultaneously at the four corners of the box.

An alternative embodiment of the needle device, designated by 1', will now be described with reference to FIG. 3. Any element identical to an element in the previous figures is designated by the same reference and will only be described if and as needed.

According to this alternative embodiment, the upper wall, designated as 10', is not rigid anymore, but consists of a material with elastic properties, or at least of a material being reversibly deformable under the action of a pressure force such as the user's weight. This wall 10' is continuous, without the above mentioned holes. The needles, designated here by 3', also are modified: each limit stop, designated by 31', also acts as an upper end of the cylindrical body 30' and rests on the lower face of the wall 10'. The needles 3' pass through bores 14 managed through the lower wall 11, and the latter plays the role of a guiding plate maintaining them in vertical direction. The device comprises side walls 12 as above, on the upper ends of which the deformable wall 10' is fixed.

When the user lays his foot 2 on the wall 10', this wall is pushed down and will in its turn, by pressing onto the limit stops 31', push down by cylindrical bodies 30' of the needles 3'. The springs associated with these needles 3' exert a restoring force, which tends to oppose the plunge of the wall 10' and thus resist to the translation downward motion of the needles 3'. As previously also, the springs 40 are calibrated. For this reason, the wall 10' will take the exact shape of the plantar arch 20 of the foot, and the set of the lower ends 301 of the needles 3' define a warped surface $S_A$ which reproduces the above mentioned profile, under the device 1'.

Acquiring this profile results from measuring the movements of the ends 301 of the needles 3' with respect to a reference plan $P_R$ (the rest position when the foot 2 does not rest on the wall 10'). The initial position, or rest position of the wall 10' is represented in FIG. 3 in dashed lines. This position is also reverted to by the wall 10' when the pressure is released (withdrawal of foot 2), under the action of both the springs 40 and the wall 10', if the latter is made of elastic material, because of the intrinsic elastic properties thereof.

Of course, stop ring 31' could as well be distant from the higher top end of the needle rod and come in abutment against a movable intermediate plate for varying the spring strength as described above.

In both alternative embodiments, the devices 1 or 1' provide an "offset" profile of the arch 20 as surface $S_A$ in a spatial place where it becomes more accessible and can easily be acquired and digitized. In other words, the surface described by the lower bottom ends of the needle rods constitutes the duplicate of the profile their upper top ends have to conform to. It should be noticed here that identical duplication involves that all rods have the same length, but that is not compulsory since the profile could as well be calculated from the individual displacement of the rods with respect to a non-planar reference profile.

According to the invention, the sensing device as above described is especially convenient for being used when detecting the position of the rods (in fact their lower ends) through optical means illuminating and observing their terminal faces, which would be impossible if operating on their upper ends.

In a first embodiment, which will now be described, the invention is implemented by a device with optical sensors. It should be noted that the shape acquisition can be directly performed due to the arrangements adopted within the frame of the invention, i.e. without having the laser beam passing through an intermediary transparent wall forming a support for the object the profile of which is to be acquired, especially the foot arch profile in the preferred application.

The profile of the surface $S_A$ is acquired by an optical sensor device arranged below the sensing needle device 1. It must be clear that the surface $S_A$ is limited. As more particularly shown in FIG. 2, it in practice is limited by the dimensions of the arch 20 of the foot 2, in other words the zone where the foot exerts a pressure onto the ends 300 of the needles 3: the hatched area surrounded by dashed lines. Outside this pressure area, the needles 3, and more precisely the upper ends 300 thereof, are not stressed. The same feature is also found below the sensing device 1: a central zone delimiting the surface area $S_A$ (a wrapped tridimensional curve) and a planar peripheral zone confounded with the reference plane $P_R$, representing the rest state.

Figure 4:
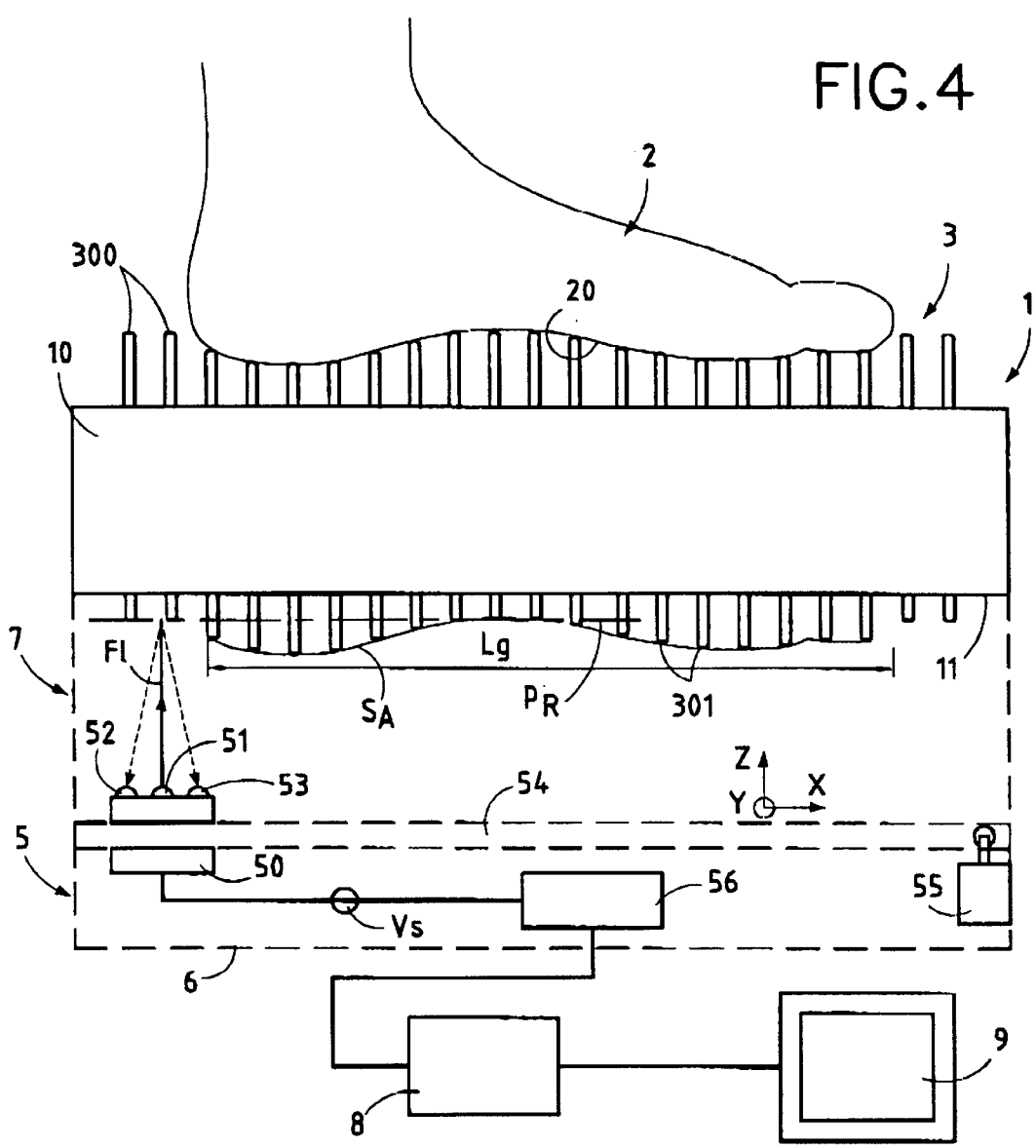
FIG. 4 illustrates a complete system for plotting the shape of a tri-dimensional object, according to the first embodiment, including an optical sensing device.

FIG. 4 illustrates an embodiment of the complete system 7 according to the first embodiment, incorporating an optical sensing device.

To simplify the drawing, only those elements necessary for a good understanding of the invention were represented. The alternative of FIGS. 1A to 2, was selected, without this limiting in any way the scope of the invention. Any element common with previous figures is designated by the same reference and will be described again only if and as needed.

The system 7 includes a sensing device 1 with needles 3 and a device with an optical sensor 5, all of which is supported by a single housing or chassis 6 (in dashed lines in FIG. 4).

Various embodiments are possible for the device 5. FIG. 4 illustrates a first embodiment possibility wherein the device 5 includes an optical sensor 50 moving linearly parallel to one of the horizontal axes of the matrix of the matrix of needles 3 of the sensing device 1, advantageously along the axis X which supposedly is parallel to the largest dimension of the housing or frame imprisoning the needles 3.

For this purpose, a driving motor 55, integral with the chassis 6, and a (non-represented) set of conventional pulleys and/or gears is provided. Such can for instance be comprises of a worm rotatively driven by the motor 55 and, in its turn, driving the sensor 50 in a translation movement parallel to the axis X. Since the measurements are discrete, as shown hereafter, a step motor type 55 can be used. The sensor 50 is arranged on a movable assembly and is guided in its translation movement along the axis X by rails 54 arranged parallel to the axis X on both sides of the sensor, and fixedly mounted on the chassis 6. According to a non-represented second version scheme, the sensor 50 could have a motor coupled to a rack or a worm, for instance, fixedly mounted on the guided rail 54 or the chassis 6. Conventional (non-represented) transducers offering at all times a knowledge of the exact position of the motor 55 along the axis X, potentially associated with detectors, could also be used.

The sensor 50 can be similar to, and even identical with, the sensor described in the above-mentioned French patent Fr-B-2 685 764, from which a more detailed description can readily be obtained. The sensor 50 essentially comprises a laser source 51 generating a lamellar beam $F_1$. The source 51 advantageously consists of a semiconductor laser diode. The sensor 50 comprises at least one camera and preferably two cameras, 52 and 53, as illustrated by FIG. 4, arranged on both sides of the laser source 51, along the movement axis of the sensor 50, i.e. along the axis X (in the described example).

The lamellar beam $F_1$ is directed towards the lower ends 301 of the needles 3. It preferably strikes the reference plane $P_R$ under a normal incidence. Advantageously, the distance between the sensor 5 and the reference plane $P_R$, and the vertex angle of the beam $F_1$, are chosen in such a way that the incident beam, which is a narrow light beam, will cover the whole width of the lower wall 11 (according to the axis Y, in the described example), whichever the amount of the plunging displacement of the needles 3 may be (potential extreme position of the ends 301 of needle 3). But of course, one can alternatively provide for a scanning movement in two direction.

The cameras 52 and 53 are inclined with respect to the axis Z orthogonal to the plane $P_R$, so as to analyze the trace of the lamellar beam $F_1$ on the ends 301 of the needles 3, under different angles. These cameras deliver electric output signals $V_S$ which are transmitted to a signal processing assembly 8. This assembly can be located either inside or, as suggested in FIG. 4, outside the housing 7. In the latter case, it advantageously can be a digital computer with a conventional recorded program, for instance a microcomputer 8 connected to a viewing member 9, such as a cathode ray tube or a liquid crystal or a plasma monitor. If the cameras 52 and 53 are of the analogic type, the signals $V_S$ must first be converted into digital signals. For this purpose, a conventional (non-represented) analog to digital converter arranged inside the chassis 6 or a customized acquisition board for analog signals, located inside the signal processing assembly 8, can be used. Cameras which directly deliver digital signals representing the sensed image also are available. The signals in this case are transmitted to a board arranged inside the assembly 8 and having an acquisition port for digital signals. The housing 7 may also include pre-processing circuits 56 which convert the output signals $V_S$ into signals conforming to a standardized protocol, before their transmission under this shape to the signal processing assembly, for instance towards a standardized "RS 232" series port.

The profile acquisition for the arch 20 of a foot 2, via the profile of the surface $S_A$ which is an image of the latter, conventionally is performed by successive slices which will be called $S_i$, where i is an arbitrary index varying for instance from 1 to a maximum $i_{max}$ value. Within the frame of the invention, each slice $S_i$ preferably represents a column (parallel to the axis Y of the rectangular matrix of ends 301 of needles 3). The slice $S_i$ more precisely represents in the described example the position of all ends 301 of needles 3 of a column indexed i of the matrix, with respect to the reference plane $P_R$, i.e. the plunging amount of the corresponding needles 3.

If N and M are the respective numbers of needles 3 per column (parallel to the axis Y) and per row (parallel to the axis X, the movement axis of the sensor 50), the maximal number of the acquired points per slice $S_i$ is N, and the maximal number of slices is $i_{max}$=M. The number of useful slices in the general case, is smaller: this depends upon the length Lg of the foot 2, where Lg is the maximal length of the arch 20 being in contact with the upper ends 300 of the needles 3 when taking into account the pitch pg between these ends (see FIG. 2) along this direction, since this measurement is discrete. Similarly, the number of useful points, for a given slice $S_i$, depends upon the width of the arch 20. The maximal number of useful points is determined with the maximal width La (see FIG. 2) of the plantar arch 20 being in contact with the upper ends 300 of the needles 3 when taking into account the pitch pa between these ends (see FIG. 2) along this direction.

The profile acquisition process for the plantar arch 20, or more generally for a tri-dimensional object exerting a pressure force on the upper ends 301 of the needles 3, will now be described in a more detailed manner.

The process includes a preliminary calibration phase. It is performed in the initial, so called "rest" conditions, i.e. without any stress being exerted upon the upper ends 300 of the needles 3. The surface $P_R$, the so called reference surface, defined by the lower ends 301 of the needles 3, is completely scanned: acquisition of M slices $S_i$ N points each, with i varying from 1 to $i_{max}$. For this purpose, the sensor 50 is driven along the axis X so as to illuminate, slice by slice $S_i$, the whole reference surface $P_R$. Since the sensor a priori should perform a return trip to revert to its initial position, an alternative possibility consists of performing a double acquisition and calculating an average of both measurement series.

When taking into account any imprecision, the reference surface substantially is represented by a plane $P_R$, the so called reference plane, but the flatness condition is not necessary since the later acquisition phase for the required profile includes a comparison step with the acquired coordinates of the reference points. The reference surface $P_R$ namely defines a reference coordinate dot chart.

This preliminary calibration phase can be performed either once for all, if it is possible to admit that the system time stability is sufficient, or at determined periods of time, or else before each acquisition. According to a preferred alternative of the invention, the sensing device 1 is removable and interchangeable, so as to allow using the same device with an optical sensor 5 for all users (whether adult, child or baby). In this case, a calibration phase must at least be performed after each replacement. The same is true when the same sensing device is retained and the spring calibration is modified instead.

The data representing the reference coordinates are translated by the processing assembly, into binary word signals, stored in a random access memory, or RAM, provided in the assembly or in a mass memory (hard disk, and so on) for later use, i.e. for the profile acquisition phase proper.

This acquisition phase includes the following steps:

a/ laying the foot 2 on the upper ends 300 of the needles 3, in a given posture (laying flat, resting on the heel, and so on) i.e. with full or partial pressure being applied;

b/ scanning with the lamellar beam $F_1$ the surface formed by the lower ends 301 of the needles 3, with the scanning being obtained by a translation movement of the sensor 50 parallel the axis X (possibly a double acquisition: return trip);

c/ acquiring M slice $S_I$ of N points each and generating output signals $V_S$ resulting from an opto-electronic conversion produced by the cameras 52 and 53, so as to plot the coordinates of the acquired points in a given measurement space; and d/ transforming the acquired and digitized data into an universal set, by comparison with the reference coordinate data belonging to the measurement space, i.e. the coordinates of the lower ends 301 when those are inside the reference plane $P_R$, so as to plot the profile of plantar arch 20.

These steps can be complemented by an interpolation and smoothing step for the coordinates of the thus acquired points, so as to obtain a profile with a continuous variation.

As previously, the acquired coordinates are translated into binary words which can be stored, in particular if the acquired signals are not immediately used but provided for a later use.

Actually, as indicated before, only the area corresponding to the surface $S_A$ needs to be acquired. In order to eliminate stray measurements caused by any geometric or other imprecision, it will be sufficient to retain a threshold below which the coordinate measurement should be discarded. In practice, the comparisons of step d/ consist of calculating, for a given needle 3, the amount of plunge of the latter with respect to its rest position (position of its lower end 301 on the reference surface $P_R$). If this amount is smaller than the above-mentioned threshold, it can be ignored, which in particular avoids taking into account points outside the area $S_A$, i.e. points actually outside the arch 20. This threshold can be predetermined or calculated from imperfections observed or measured during the calibration phase. As an example, the threshold could be determined by calculating the maximum error value which would allow an assimilation of the reference surface $P_R$ with a plane. The obtained measurement precision during the acquisition is at most equal to the thus adopted or calculated threshold value.

The acquisitions of the profile of the arch 20 for other postures of the same foot 2 (on the heel, on the foot tip, and so on), or of the other foot of the user are easily performed by repeating the previous acquisition steps. Performing a calibration phase between each acquisition series generally is not needed.

The acquired data, in addition to being stored, can be displayed on the viewing member 9, practically in real time, after the end of the scanning step b/. This displaying can be performed in a well known manner per se, in any convenient way: under the shape of the so called "filar" display for instance or, if an interpolation smoothing step is performed, the shape of an tri-dimensional surface with continuous variation, which can be rotated in space, with the help of adequate display programs, available off the shelf.

Finally, in the preferred application of the invention, the acquisition data available under a digital shape can be used during a final phase, in a direct or delayed manner, for digitally controlling a machine tool producing orthopaedic shoe components, in particular the integrated sole of such shoes, or an orthopaedic sole to be inserted into a conventional shoe. This phase can be implemented either in situ or remotely. In such a case, the data can be transmitted by computerized communications (local area network, internet, etc.) or can be recorded on an intermediary medium (disc, magnetic band, and so on).

Figure 5:
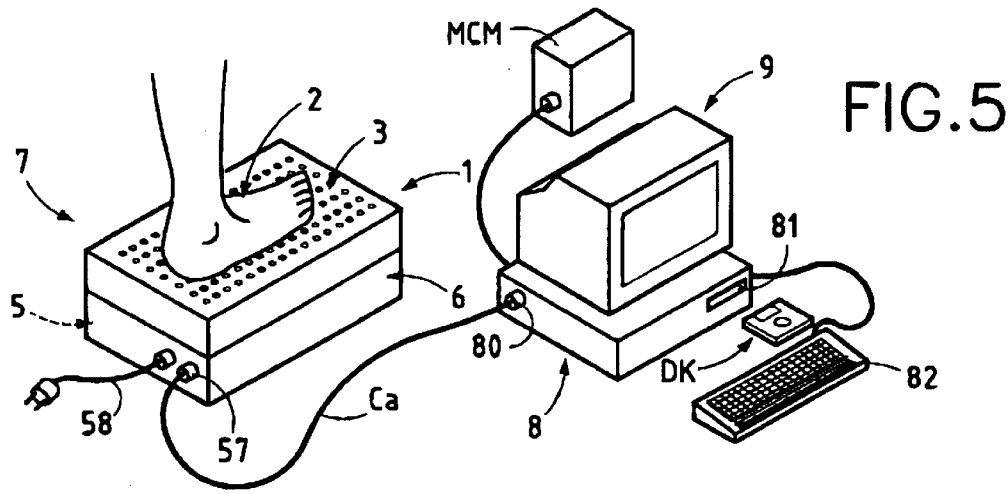
FIG. 5 illustrates a practical embodiment of the system of FIG. 4.

FIG. 5 illustrates an example of a practical embodiment of the plotting system according to FIG. 4.

The acquisition system 7 comprises the device 5 with an optical sensor (FIG. 4: 50) and the sensing device 1 with the needles 3, within the same enclosure 6. The sensing device 1 preferably is removable, as indicated previously. Preferably also, the electric power supply necessary for the cameras and the laser source, as well as for a potential preprocessing circuit (FIG. 4: 56) is independent and brought in by a mains cable 58. The various sources for the electrical voltages needed for the proper operation of these members also are provided.

In the example illustrated in FIG. 5, the plotting system 7 properly said is independent from the signal processing assembly consisting of a microcomputer 8, which allows transporting it easily. The link with the microcomputer 8 consists of a simple cable Ca, for instance its first end with the connector 57 of the housing 6 and at a second end with a connector 80 of the microcomputer 8. The microcomputer 8 is coupled to a viewing member, or monitor, 9 and to a data and/or instructions entry keyboard 82. It includes the conventional circuits for this type of equipment: random access memory, central unit, mass memory (hard disk), compact disk drive, and so on, non-represented in the figure. It also includes a reader/recorder 81 for discs DK, on which all or part of the acquired and digitized data can be recorded. The programs, whether or not specific, necessary for the proper operation of the microcomputer 8 are loaded by means of diskettes, a compact disk or direct downloading from a local area network or an external network (internet, intranet, and so on). The digitalization can be performed, either directly by means of the circuits included in the chassis 7 (FIG. 4: 56) or by a specialized board of the microcomputer 8, which receives the data under an analog form through the cable Ca.

The microcomputer 8 performs all signal processing operations necessary for shape acquisition, but also transmits order signals to the sensor 50 (FIG. 4) and its motorization circuits, in particular for performing the various scanning operations needed for the calibration and data acquisition phases: back and forth sensor movement (FIG. 4: 50) along the axis X, between a rest or initial position and a stroke limit or final position. The order signals also can transmit through the cable Ca, for instance as serial binary signals. In such a case, the chassis 6 must include circuits (FIG. 4: 56) adapted to recognize the signals transmitted by the microcomputer 8 and convert them into order signals usable by the various sensor components: digital and/or analog signals. The microcomputer 8 also receives, via the cable Ca, data related to the sensor position along the axis and, more generally, the operating state of the various members included in the chassis 6.

The microcomputer 8 finally can order, via a customized or standard interface device, a digital control machine MCN or similar for producing orthopaedic shoes or soles or, more generally, to reproduce the tri-dimensional object the profile of—at least part of—a surface of which was acquired. The microcomputer 8 can be linked to this MCN machine by a simple cable or via a transmission network.

It should be clear that the data representing the acquired coordinates can be modified by a specific program or manually by a operator (with the help of the keyboard 82, for instance), before any transmission or recording on a diskette DK. In other words, the object is not compulsorily a reproduction of the plotted profile, but can be derived from this profile. It namely can be desirable to introduce corrections, of a time evolutionary type, notably for orthopaedic soles, in order to obtain an adjustment of the observed malformations. In the latter case, a history of the performed corrections and the obtained results on a patient with malformations can be saved in a memory.

Two additional embodiments of the shape acquisition and digitalization device cooperating with the needle box will now be described. This box remains unchanged, and any of the versions described with reference to FIG. 1A to 3 can be operated.

In a first additional embodiment, described with reference to FIGS. 6A to 6C, an imaging device based on a digital photo-camera or a digital video camera is operated. This equipment is designated by CN on FIG. 6A.

To simplify the present disclosure, the sensing device 1 supposedly, without this limiting in any way the invention, is in accordance with the first version, i.e. the one described with reference to the FIGS. 1A to 2 and consequently will not be described again. The needles 3 also supposedly are in the rest state. Their lower ends 301 define as prevsiously a reference surface, advantageously a reference plane $P_R$.

These ends 301 of the needles 3 are illuminated by at least one white light source, advantageously by two symmetrical sources $L_1$ and $L_2$, under an inclined incidence. When they are thus illuminated the terminal faces of the needles 3 are shining. They have reflecting surfaces for that purpose. The photo-camera CN consequently observes a plurality of brilliant points that have same intensity and are regularly spaced as are the needle rods. The light density is substantially homogenous on the whole reference surface $P_R$, in particular if this reference surface is planar. The average incidence angle of the light rays emitted by the light sources $L_1$ and $L_2$, with respect to the reference plane $P_R$, typically is included in the range from 3 to 60 degrees.

The camera CN converts the brilliance of each point into a series of electrical output signals, of a digital type. Those signals are transmitted by a link 830 to a digital acquisition board 83, arranged inside the signal processing assembly having a pre-recorded program, advantageously a microcomputer similar to the microcomputer 8 of FIG. 5. The link 830 can for instance be of a serial type.

The image formed by the camera CN can be displayed on the monitor 9 of the microcomputer 8, for instance under a "raw" shape, as suggested by FIG. 6B. The image 90A reproduced on the monitor 9 will then consist of a set of points displayed with the same light intensity, symbolized by white circles on FIG. 6B. This image 90A represents the rectangular surface of the reference plane $P_R$. Each point displayed on the monitor represents one of the ends 301 of the needle 3.

When a foot is laid upon the upper ends 300 of the needles 3, as illustrated in FIG. 1B, the needles will plunge, to a larger or a smaller extend depending upon their position in the matrix. The light density of the surface defined by the lower ends 301 of the needles 3 is not homogenous anymore, in particular for the surface $S_A$ limiting the resting zone of the foot 2. The density varies in correlation with the amount of plunge of the needles 3. The incident angle of the light emitted by sources $L_1$ and $L_2$ on the surfaces of the needle ends will namely vary depending upon the amount of plunge, which will modify the light reflection on these surfaces.

The points constituting the image 90B displayed on the monitor 9 now have variable light intensities, as shown by FIG. 6C. To illustrate the invention method, only two light intensity values, respectively illustrated by white circles $900_L$ and black circles $901_L$ are represented. In fact, a much finer graduation of light intensity values is obtained, comprised between a maximal light (representing, for instance, the rest state: FIG. 1A) and a minimal limit (represented by a maximal plunge of a needle 3: FIG. 1B).

A conventional image processing software, available off the shelf, allows further determining the contour of the characteristic surface $S_A$ of the support surface of the foot 2. Various schemes are known. The light intensity gradients from one point to another can be calculated for this purpose, and the above mentioned contour can then be determined from this calculation. Namely, the light intensity fluctuations outside the surface $S_A$ are, either non-existent, or at least lower than a determined threshold. The light intensity amount is directly derived from the digital signals output by the camera CN.

Similarly, inside this contour $S_A$, the same software can determine the plunge state by performing a correlation between the light intensity acquired for a given needle 3 and the amount of its plunge. The correlation coefficient can be determined by initial calibration. A first reference is obtained in the rest state (with the reference plane $P_R$ being illuminated). On or more other references can be obtained by plunging, in a known and homogenous way, the set of needles 3, for instance with the help of a planar object.

By means of these different determinations, a tri-dimensional model of the surface $S_A$ can easily be constructed, isolated from the other acquired points (zone outside the surface $S_A$) and, as previously, displayed under a "filar" or a "smoothed" form. These operations can be performed under software conduct.

The acquired data finally can be used in real time and/or be recorded for later use, or be downloaded. These steps of method strictly are the same as those described with reference to FIG. 5.

According to a second additional embodiment, described with reference to FIGS. 7A and 7B, a telemetry device is implemented. This embodiment itself has several versions.

Figure 7A:
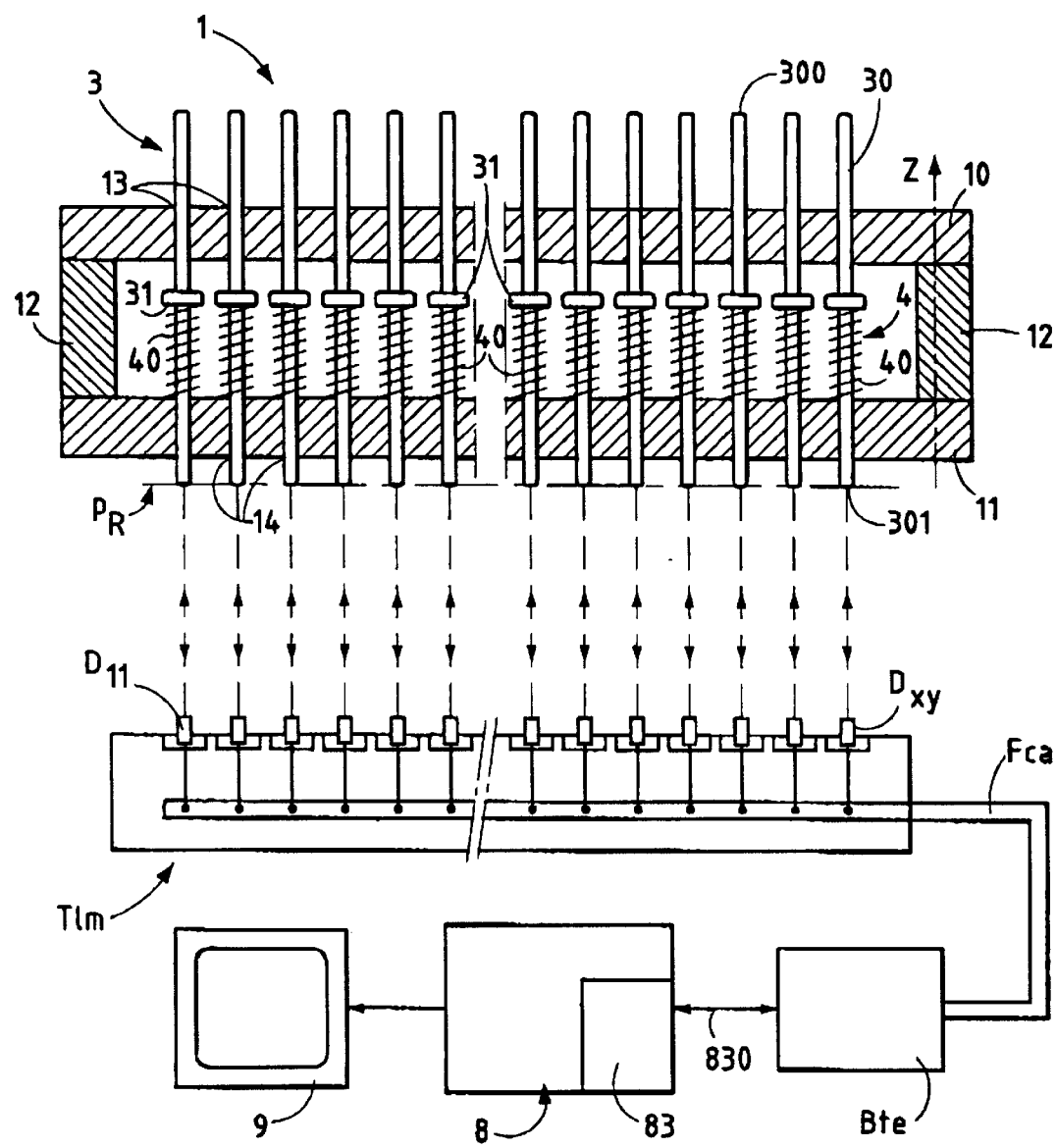
FIGS. 7A and 7B illustrate a shape acquisition and digitalization device according to a second additional embodiment; and according to two versions.

According to the first version of this second additional embodiment, as illustrated by FIG. 7A, the telemeter Tlm includes a matrix of opto-electronic elements comprising semiconductor laser diodes, each of which is associated with a photo-conductive element. The pairs of opto-electronic elements are referenced $D_{11}$ $D_{xy}$.

It has been considered that the sensing device 1 as previously is of the type represented on FIGS. 1A to 2, without this in anyway limiting the invention. This device 1 furthermore was represented in the rest state with the lower ends 301 of the needles 3 defining a reference plane $P_R$ in this state.

The telemeter device is arranged below the needle box 1. The number of the laser diodes of the matrix pairs $D_{11}$ to $D_{xy}$ is equal to the number of needles 3, with x and y being equal to the number of rows and columns of the needle matrix 3. The laser diodes of the pairs $D_{11}$ to $D_{xy}$ are spatially arranged in the same way as the needles 3. The total number of diodes consequently is equal to the product xy. Any particular laser diode, for instance the diode of the pair $D_{mn}$ (with m and n being arbitrary indexes, smaller than or equal to x and y, respectively), emits a collimated beam parallel to the axis Z, directed towards the lower end 301 of the needle 3 facing it, which beam is reflected on the terminal face of the needle 3. Since the position of the laser diodes of the pairs $D_{11}$ to $D_{xy}$ is spatially fixed, the distance, between this end 301 of the particular needle 3 and the laser diode of the pair $D_{mn}$ illuminating it, is easy to determine. The photo-conductive element associated to each laser diode of the pair $D_{mn}$ converts the reflected light into an electric signal transmitted through a cable beam fca to the electronic circuits Bte, schematically represented under the shape of a housing. These electronic circuits Bte control an electronic scanning of the various laser diodes of the pairs $D_{11}$ to $D_{xy}$, for instance a television type scanning. The output signals delivered by the matrix are converted by these very same circuits Bte into digital signals and transmitted, via an output link 830, to a digital acquisition board 83, similar to the board having the same reference in figure 61. This board is arranged (in the described example), within a microcomputer 8, in particular equipped with a monitor 9.

When the foot 2 rests upon the upper ends 300 of the needles 3 (see FIG. 1B), the needles 3 will plunge, to a larger or a smaller extent, according to the process already described. The telemeter Tlm directly measures the movements of the needles 3, i.e. the variations of the distances between the lower ends 301 of the needles 3 and the corresponding laser diodes of the pairs $D_{mn}$. The output signals and the signals transmitted on the link 830 are directly representative of the amounts of plunge. The scanning management can be controlled by the microcomputer 8.

It thus is possible, after an initial calibration, to display as previously on the monitor 9 the tri-dimensional surface $S_A$. This displaying is performed with the help of a conventional image processing software. As previously, the acquired measurement signals can, either be used directly and/or be recorded or else be transmitted remotely.

Figure 7B:
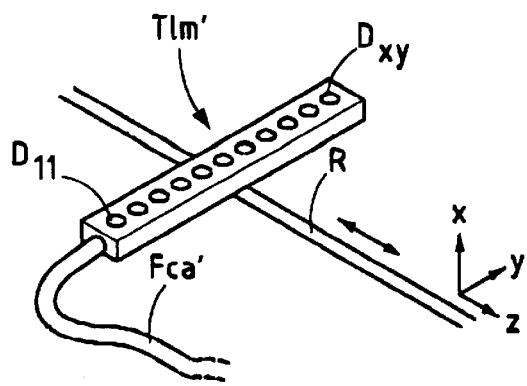

According to a second version of this additional embodiment, illustrated by FIG. 7B, the telemeter, shown as Tlm', includes a simple bar of laser diode pairs and photo-conductive elements $D_{11}$ to $D_{1y}$, arranged parallel to one of the axes of the matrix of needles 3, for instance the axis Y. The number of laser diodes is equal to the number of rows in the matrix of needles 3. This bar of laser diodes and of photo-conductive elements $D_{11}$ to $D_{1y}$ is driven by a (non-represented) motorization means similar to those of FIG. 4, along axis X. This translation movement is guided by one or more rails R, so that the bar stays parallel to the axis Y. The motorized means may advantageously include a step motor. At each translation movement "step", a column of points is acquired, i.e. the distances between the diodes and the lower ends 301 of the needle column 3 facing them. When all columns of the matrix of needles 3 have been scanned, the acquisition process is finished. The mechanical scanning parallel to the axis X can be performed in either direction. The output signals of the telemeter Tlm' are transmitted, at each acquisition step, i.e. for all needles of a row, by a cable bundle fca' to a (non-represented) electronic housing, as previously. The digitalization and use schemes of the acquired measurement signals are quite similar to what was previously described. The management of the electronic and mechanical scanning operations can be performed under control of the microcomputer 8.

According to a still other, non-represented version, the bar of diodes and photo-conductive elements, $D_{11}$ to $D_{1y}$, is fixed. A deflection of the laser beams is performed in oder to obtain a scanning of the lower ends 301 of the needles 3.

Several conventional telemetry schemes can be used. According to the invention, and in all three just described versions, the telemetry advantageously is based on the emission of a light impulsion train, with return trip time measurements, which allows determining distances when the light propagation speed is known.

Finally, the optical telemeter can be replaced by a magnetic telemeter. It then is necessary for the needles 3 to be made of a material exhibiting magnetic properties (steel for instance).

Upon reading the above, it is easy to ascertain that the invention does reach its aims.

It however should be clear that the invention is not limited to the only embodiments explicitly described, in particular with reference to FIGS. 1 to 7.

In particular, instead of helicoidal springs 40, it is possible to use similar members showing elastic counteracting properties so that they are able to oppose to the plunging movement of the needles a resisting force that can be varied and adjusted, thereby providing means for a varying calibration depending upon the user's weight.

Although the circular cross section rods are particularly adapted for realizing a needle box, since the holes or bores for their passage through the plates or walls closing the support bow are particularly simple to make in this case, it is quite conceivable to use other shapes. In particular, rods with a square, rectangular or hexagonal cross section can be provided.

The materials, which can be used, are essentially linked to the specific application forecast and are part of a simple technological choice for those skilled in the art.

Similarly, the numerical examples only were given in order to better illustrate the invention.

It also should be clear that, although the invention is particularly adapted to the production of orthopaedic shoes and soles, it is not, by any means, limited only to this type of applications. It is related to the plotting of at least one surface portion of any tri-dimensional object, inasmuch as it can rest, by virtue of its own weight or by external means, on the face which was called upper face of the sensing device, and inasmuch as the portion of the above surface does not extend beyond the dimensions of a frame delimiting the needle matrix. It also has been seen that the sensing device could be adapted to various object weights (and pressure forces) by modifying the calibration of the springs or similar members. Thus, the system according to the invention can be of use in any technical field where the mould of a part must be produced.

The entire disclosure of all applications, patents and publications, cited above, and of corresponding French application No. 9804981, filed Apr. 21, 1998 is hereby incorporated by reference.

What is claimed is:

1. A system fo plotting the profile of a tri-dimensional object, comprising a sensing device comprising a matrix of rods movable across a support for receiving said object onto a first top end of each said rods under a determined pressure force, thereby driving said rods in a translation motion through a distance varying from one rod to another depending on said profile shape so that the second bottom ends of said rods define together a surface duplicating said profile shape to be plotted, resilient means being associated with said movable rods to oppose a predetermined resisting force opposing said pressure force, for acquiring and digitalizing said surface duplicating said shape to be plotted, wherein said device delivers output electric signals correlated with the space coordinates of said second end of said rods with respect to reference coordinates defined by the position taken by the rods in a rest state.

2. A system according to claim 1 for use in plotting the shape of a plantar arch of a foot constituting said tridimensional object.

3. A system as claimed in claim 1, wherein said support of the sensing device consists of a needle box having main planar mutually parallel first and second walls, each with holes through which the bodies of said rods are slidably mounted, whereby said rods are guided and protrude on both sides of said box, and lateral walls or spacers maintaining the distance between said first and second main walls.

4. A system as claimed in claim 1, wherein said support of the sensing device consists of a needle box having main planar mutually parallel first and second walls, wherein said first main wall is continuous and made of a material deformable under the action of a pressure force, said first main wall resting in contact with said first top ends of said rods, and wherein said second wall has bores for guiding said rods in slidable relation therethrough, while they protrude by their second bottom ends from said box and said second wall, and lateral walls or spacers maintaining said first and second main walls together.

5. A system as claimed in claim 1, further comprising means to adjust the strength of said resilient means so as to vary said resisting force opposed to the movement of said rods due to said pressure force.

6. A system in accordance with claim 2, further comprising means to adjust the strength of said resilient means to anyone of predetermined values of said resisting force for selection depending upon the weight of the user as representative of said pressure force.

7. A system as claimed in claim 1 wherein said resilient means consist of calibrated springs that are realized as helicoidal spring wound coaxial to said rods and compressed between a fixed plate guiding said rods and individual stops provided on each said rod.

8. A system as claimed in claim 1, wherein said rods are arranged according to the rows and columns of a rectangular matrix.

9. A system as claimed in claim 2, comprising interchangeable distinct sensing devices for alternate use with a same acquisition device, depending upon the weight of the persons the foot arch of which must be plotted, said sensing devices differentiating from one another by calibration values of calibrated springs that constitute said resilient means.

10. A system in accordance with claim 1, wherein said support of the sensing device comprises at least one fixed wall guiding bores through which said sensing rods are slidably mounted and from which they protrude at their second bottom ends, and wherein said resilient means consist of calibrated springs realized as helicoidal spring wound coaxial to said rods and compressed between said fixed wall guiding said rods and individual stops provided on each said rod, and further comprising means to adjust the strength of said resilient means depending upon the weight of the persons the foot arch of which must be plotted, said adjusting means comprising a movable intermediate plate on which said stops are in abutment.

11. A system in accordance with claim 1 wherein said acquisition device comprises an optical sensor having at least one laser source generating a lamellar beam forming a measurement laser plane directed towards the surface determined by said lower bottom ends of rods, means for moving said lamellar beam in a scanning movement over them, and at least one opto-electronic camera for analyzing the trace of said beam on the scanned bottom ends of rods and delivering output signals representing their coordinates.

12. A system as claimed in claim 11 wherein said rods are arranged according to the rows and columns of a rectangular matrix and said optical sensor is mounted on a movable assembly moving along a predetermined axis parallel to the rows or the columns of said matrix, said scanning means comprising a motor for driving said optical sensor along said axis.

13. A system according to claim 1 wherein said acquisition device comprises at least one light source for illuminating said lower bottom ends of said rods and a camera delivering digital output signals representing the light intensity of the light reflected by terminal faces of said bottom ends, and further comprising electronic circuits for determining the amplitude of said translation movements of the rods as calculated from the variations of said light intensity between their rest position and their position after they have been driven down by the action of said determined pressure force.

14. A system according to claim 1 wherein said acquisition device comprises optical telemeter means arranged facing reflective terminal faces of said lower bottom ends of said rods for detecting the distance from each of them and delivering output electric signals representing the distances detected.

15. A system according to claim 14 wherein said rods are arranged according to the rows and columns of a rectangular matrix and said telemeter means comprise a matrix of opto-electronic elements with semiconductor laser diodes, provided in a number equal to the number of the rods in said matrix and spatially arranged in a manner identical to these rods, and photoconductor members, each of which is associated to one of said laser diodes, for delivering output signals representing the distance measured using a measuring beam emitted towards each of said lower bottom ends of said rods from said laser diodes.

16. A system according to claim 14 wherein said rods are arranged according to a rectangular matrix of rows and columns parallel to respective orthogonal reference axes and said telemeter means comprise a bar of opto-electronic elements with semiconductor laser diodes arranged parallel to a first of said reference axes identically as a same number of rods in said matrix parallel to said first reference axis, and photoconductor members, each of which is associated to one of said laser diodes, for delivering output signals representing the distance measured using a measuring beam emitted towards each of said lower bottom ends of said rods from said laser diodes, while said bar is moved along the second of said reference axes by scanning means so as to acquire the coordinates of all lower ends of the rods in said matrix.

17. A system as claims in claim 16 wherein said contactless acquisition device is linked by a bi-directional data transmission link with a signal processing unit comprising a computer with a recorded program for transforming said output signals into digital data representing said coordinates of the plotted shape and transmitting order data to said acquisition device, said computer further comprising storing means for said digital data and display means for said data, said system further comprising means for exploiting said digital data calculated by the computer and deriving said shape therefrom.

18. A system as claims in claim 15, wherein said contactless acquisition device is linked by a bi-directional data transmission link with a signal processing unit comprising a computer with a recorded program for transforming said output signals into digital data representing said coordinates of the plotted shape and transmitting order data to said acquisition device, said computer further comprising storing means for said digital data and display means for said data, said system further comprising means for exploiting said digital data calculated by the computer and deriving said shape therefrom.

19. A method for producing an orthopaedic shoe or sole using the system as claimed in claim 1, comprising laying a foot on said sensing device with the plantar arch pressing on said upper top ends of the rods, thereby exerting said pressure force, using said contactless acquiring device to acquire a dot chart of points and digitize them into digital data representing the coordinates of said acquired points in a determined measurement space, transforming said data into an absolute referential by comparison with reference coordinate data belonging to said measurement space, so as to plot the profile of the plantar arch, and operating a digital control machine tool controlled by said acquired and digitized data representing said profile of the plantar arch for producing said shoe or sole as a tri-dimensional object such that part of the surface thereof is derived from said data.

20. A method as claimed in claim 19, further comprising a preliminary calibration step of said contactless acquisition device by plotting the coordinates of said lower ends of the rods while they are in said rest state in which the upper ends are not submitted to said pressure force, whereby the set of lower ends in said rest state define a reference surface in said measurement space.

21. A method as claimed in claim 20, comprising an additional calibration step consisting in adjusting the strength of said resilient means resisting to the downward translation of said rods depending upon the person whose foot is to be plotted.

* * * * *